US008077940B2

(12) United States Patent
John et al.

(10) Patent No.: US 8,077,940 B2
(45) Date of Patent: Dec. 13, 2011

(54) METHOD FOR RECONSTRUCTING A THREE-DIMENSIONAL TARGET VOLUME IN REALTIME AND DISPLAYING IT

(75) Inventors: Matthias John, Nürnberg (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 978 days.

(21) Appl. No.: 11/725,830

(22) Filed: Mar. 20, 2007

(65) Prior Publication Data

US 2007/0233739 A1    Oct. 4, 2007

(30) Foreign Application Priority Data

Mar. 23, 2006    (DE) .................. 10 2006 013 474

(51) Int. Cl.
*G06K 9/00* (2006.01)
(52) U.S. Cl. ........................... 382/128; 382/100
(58) Field of Classification Search ................ None
See application file for complete search history.

(56) References Cited

U.S. PATENT DOCUMENTS

| | | | | |
|---|---|---|---|---|
| 5,462,244 A | * | 10/1995 | Van Der Hoek et al. | 246/122 R |
| 5,490,075 A | * | 2/1996 | Howard et al. | 701/226 |
| 5,590,217 A | * | 12/1996 | Toyama | 382/104 |
| 5,612,699 A | * | 3/1997 | Yamada | 342/70 |
| 5,912,720 A | * | 6/1999 | Berger et al. | 351/206 |
| 5,961,571 A | * | 10/1999 | Gorr et al. | 701/207 |
| 6,321,024 B1 | * | 11/2001 | Fujita et al. | 386/281 |
| 6,470,208 B1 | * | 10/2002 | Woodford et al. | 600/428 |
| 6,909,769 B2 | * | 6/2005 | Bruder et al. | 378/8 |
| 6,995,765 B2 | * | 2/2006 | Boudier | 345/428 |
| 7,050,531 B2 | * | 5/2006 | Hebecker et al. | 378/8 |
| 7,302,286 B2 | * | 11/2007 | Camus et al. | 600/407 |
| 7,715,603 B2 | * | 5/2010 | Niethammer | 382/128 |
| 2003/0199748 A1 | * | 10/2003 | Camus et al. | 600/407 |
| 2003/0221027 A1 | * | 11/2003 | Chang et al. | 710/22 |
| 2004/0125984 A1 | * | 7/2004 | Ito et al. | 382/103 |
| 2004/0131156 A1 | * | 7/2004 | Hebecker et al. | 378/98.11 |
| 2004/0172655 A1 | * | 9/2004 | Nishiyama et al. | 725/97 |
| 2005/0036660 A1 | * | 2/2005 | Otsuka et al. | 382/104 |
| 2005/0073585 A1 | * | 4/2005 | Ettinger et al. | 348/155 |
| 2005/0110880 A1 | * | 5/2005 | Parulski et al. | 348/231.5 |
| 2005/0134710 A1 | * | 6/2005 | Nomura et al. | 348/240.99 |
| 2005/0231601 A1 | * | 10/2005 | Higuchi et al. | 348/207.99 |
| 2006/0017694 A1 | * | 1/2006 | Shikata | 345/158 |
| 2006/0061570 A1 | * | 3/2006 | Cheryauka et al. | 345/424 |
| 2006/0149425 A1 | * | 7/2006 | Davis | 701/1 |
| 2006/0152935 A1 | * | 7/2006 | Petkov | 362/459 |
| 2006/0167839 A1 | * | 7/2006 | Lind et al. | 707/2 |
| 2006/0177098 A1 | * | 8/2006 | Stam | 382/104 |

(Continued)

FOREIGN PATENT DOCUMENTS

| | | |
|---|---|---|
| DE | 101 19 228 A1 | 12/2002 |
| DE | 102 10 650 A1 | 10/2003 |
| DE | 102 45 670 A1 | 4/2004 |

*Primary Examiner* — Jingge Wu
*Assistant Examiner* — Avinash J Yentrapati (57) ABSTRACT

The invention relates to a method for reconstructing a three-dimensional target volume, particularly within the human body, in realtime and displaying it, with a three-dimensional reconstruction volume being determined from a basic set comprising a minimum number of two-dimensional images obtained from an image recording device located within the target volume, wherein, when a new image is included in the basic set, locally limited updating at least of the reconstruction volume's partial areas covered by the new image will under a predefined condition be performed and the updated reconstruction volume will be displayed.

17 Claims, 5 Drawing Sheets

U.S. PATENT DOCUMENTS

| | | | |
|---|---|---|---|
| 2006/0188067 A1* | 8/2006 | Niethammer | 378/128 |
| 2006/0198603 A1* | 9/2006 | Yao et al. | 386/68 |
| 2006/0200307 A1* | 9/2006 | Riess | 701/207 |
| 2006/0221779 A1* | 10/2006 | Matsushita et al. | 369/30.01 |
| 2006/0253028 A1* | 11/2006 | Lam et al. | 600/459 |
| 2007/0253597 A1* | 11/2007 | Utida et al. | 382/104 |
| 2008/0118108 A1* | 5/2008 | Sharon et al. | 382/103 |

* cited by examiner

METHOD FOR RECONSTRUCTING A THREE-DIMENSIONAL TARGET VOLUME IN REALTIME AND DISPLAYING IT

CROSS REFERENCE TO RELATED APPLICATIONS

This application claims priority of German application No. 10 2006 013 474.5 filed Mar. 23, 2006, which is incorporated by reference herein in its entirety.

FIELD OF THE INVENTION

The invention relates to a method for reconstructing a three-dimensional target volume, particularly within the human body, in realtime and displaying it, with a three-dimensional reconstruction volume being determined from a basic set comprising a minimum number of two-dimensional images obtained from an image recording device located within the target volume.

BACKGROUND OF THE INVENTION

Especially in the medical sphere it is important while hollow organs in the human body, particularly the heart, are being examined or treated to obtain a three-dimensional visualization of areas of the hollow organ requiring to be examined, specifically a visualization of the kind that can only be produced using an image recording device inserted into the target volume within the hollow organ. Apart from tissue types, blood flow, or further catheters inserted or, as the case may be, the catheter borne by the image recording device, the details of interest can therein also be anomalies such as, for instance, lesions caused by ablating.

When a specific number of two-dimensional images have been recorded, a three-dimensional reconstruction volume can be reconstructed from said minimum number of images. The updating frequency of said reconstruction volumes is, though, relatively low because reconstructing requires the minimum number of two-dimensional images to be present. Triggering, in particular ECG triggering, using the corresponding physiological parameter is necessary particularly for recordings of moving hollow organs, for example the heart. However, only a limited number of images can be recorded during a specific phase of motion, for example of the heart. Since from 10 to 100 images are required for creating a reconstruction, depending on its accuracy, several cycles of motion may be necessary for recording the minimum number of images.

If it is wished to show a change over time within the target volume, for example a movement therein, caused in particular by a medical instrument, or an intervention being performed within the target volume, then the minimum number of two-dimensional images will have to be recorded again, after which a new three-dimensional reconstruction volume will be displayed. A lengthy and possibly critical period of time may, though, have elapsed by then, particularly when triggering is used.

SUMMARY OF THE INVENTION

The object of the invention is hence to disclose a method enabling faster and more up-to-date displaying, particularly when changes occur within the target volume.

To achieve said object it is inventively provided in a method of the type mentioned in the introduction for locally limited updating to be performed, under a predefined condition when a new image is included in the basic set, at least on the partial areas of the reconstruction volume covered by the new image(s) and for the updated reconstruction volume to be displayed.

With the inventive method, two-dimensional images are continuously recorded in realtime, possibly with triggering, at different positions and orientations within the target volume. The image recording device must therein be moved such that good coverage of the target volume will be achieved. That can be done automatically or manually.

The inventive method can best be envisaged as two parallel, independent processes running simultaneously. Two-dimensional images are firstly continuously recorded and stored. What the invention now proposes is, in a parallel process, to update the reconstruction volume in the partial areas or, as the case may be, the area surrounding them, for which new images are already available. The idea is based on its not being necessary to re-calculate the three-dimensional reconstruction volume in its entirety when a new image or new images is/are recorded within a specific area, but its instead being possible to restrict re-calculating to the partial areas actually covered and, where applicable, the area surrounding them, thereby saving computing time and achieving a faster updating rate. The most up-to-date two-dimensional images will consequently always be used for updating the reconstruction so that overall reconstructing will basically take place step-by-step or incrementally. The overall reconstruction volume will hence be at least partially more up-to-date than when the reconstruction volume is each time completely reconstructed afresh based on new two-dimensional images. If the two-dimensional images are recorded fast enough and if the reconstruction volume is updated fast enough, then even realtime 3D imaging will be possible with the aid of the inventive method through incrementally updating the three-dimensional volume. In particular, ECG triggering can, where applicable, therein be dispensed with and it will even be possible to image a movement of the target volume in the three-dimensional reconstruction volume.

The recorded images can expediently be filed in a memory, and a defined subset of the images filed in the memory area can be selected as the basic set. A distinction must therein be made within the scope of the present invention between the memory and the basic set. The memory contains a specific number of images not all of which are necessarily yet or still contributing to the current reconstruction volume. The basic set includes the images being fed into the current reconstruction volume. It is thus inventively provided for both the above-cited processes, namely the recording and storing process and the reconstructing process, to access a common, dynamically designed memory whose size can expediently be adjusted while the method is being applied. Said memory thus contains at least all the newly recorded images as well as the basic set of images being used for the current reconstruction volume. The images in the memory can especially advantageously be filed in a structured list, structured in particular according to time of recording. The images will then form a chained list from which subsets can particularly easily be taken.

In a particularly advantageous embodiment of the method the memory is embodied as a ring buffer. When a new image is recorded, another image—in the case of a chronological structure, the oldest image present—will therein be automatically deleted and overwritten at the position of the ring buffer's write pointer. The total number of images stored is predefined by the number of storage locations in the ring buffer, and the ring buffer's size can be dynamically changed by increasing or decreasing said number of locations. In particular, the basic set can be selected as a sequence of images filed in a specific section of the ring buffer or in a section thereof that can be specified based on information about the new images. Alongside the write pointer, a read pointer is provided starting from which the basic set is formed from a specific number of images.

It can also generally be provided for the basic set and/or memory to contain a fixed number of images, in particular, on said fixed number's becoming available, for an image, particularly the oldest, always to be removed from the basic set and/or memory when a new image is added. The number of images being fed into the reconstruction or, as the case may be, the number of stored images is therein advantageously kept constant. A basic set having a fixed number of images will insure that images that are too old can no longer compromise the reconstruction volume's up-to-dateness during updating and when interpolating is in progress. Keeping the images stored in the memory constant will insure that the memory's capacity is evenly utilized.

An up-to-date three-dimensional reconstruction volume depends not only on the most recent images' always being fed in but also on whether out-of-date information is removed from the reconstruction volume. That is why provision is also preferably made for, under a further condition when an image has been eliminated from the basic set, performing locally limited updating at least of the reconstruction volume's partial areas covered by the eliminated image(s) and displaying the updated reconstruction volume. A distinction is therefore made here between two possibilities. On the one hand, only the corresponding reference can be removed when an image has been eliminated, with the image data remaining in the reconstruction volume until updating is performed based on a new image recorded there or nearby, and the eliminated image then no longer being considered during the interpolation. It is, though, alternatively also advantageously possible within the scope of the invention for updating, in particular a new interpolation, also to take place in the area of the eliminated image already upon elimination. Out-of-date image data will then consequently not remain long in the reconstruction volume even if no more new images have been recorded in the relevant partial area or, where applicable, the area surrounding it. That, too, will consequently contribute to the reconstruction volume's being up-to-date.

An expedient condition or, as the case may be, further condition for updating can be a specific number of new or eliminated images. It can in particular be provided in an especially up-to-date variant for updating to take place whenever a new image is recorded or an image is eliminated. According to the invention it can, though, also be provided for the reconstruction volume to be updated whenever, for example, four new images have been recorded. The same can be done in the case of four eliminated images. A particularly high degree of up-to-dateness will, though, be achieved if updating takes place whenever a new image is recorded and, where applicable, an image is eliminated. That updating condition can be made even more specific. Frequently only changes within a specific subvolume of the target volume, for example in the vicinity of a medical device operating within the target volume, are of interest. It can then be provided for only images whose coverage area lies at least partially within the defined subvolume of the target volume, in particular in the vicinity of the medical device operating within the target volume, the position of which device is determined, to be counted for counting new or, as the case may be, eliminated images. In the case of a medical device, said special subvolume can move over time in parallel with the medical device's position, which can be determined by means of, for example, a locating or navigating system. An ablating intervention on the heart can be cited as a pertinent instance. That entails inserting a catheter having an image recording device into the heart as well as an ablation catheter, then by means thereof selectively obliterating areas of tissue responsible for cardiac rhythm disturbances by applying high-frequency currents. That causes what are termed lesions that will be visible in the images recorded by the image recording device. To determine whether the lesions have been produced fully as intended it will, of course, be particularly helpful for the reconstruction volume to be updated within the area in which the ablation catheter is presently operating. That can advantageously be achieved by means of the inventive method.

As an alternative to counting the recorded or, as the case may be, eliminated images it is, of course, also possible for the condition or further condition to be the elapsing of a specific period of time and for updating to take place only when images have been newly recorded or eliminated within the target volume. That variant thus provides for regular updating that is independent of the number of newly recorded or, where applicable, eliminated images but which will not, of course, take place if no new images have been recorded or none have been eliminated.

When the partial areas of new images are being updated, the image data present in the reconstruction volume's area covered by the new image(s) can be replaced with the corresponding image data of the new image(s). So with this fundamental type of updating, precisely those locations will be updated at which new, more up-to-date original image data is available from a two-dimensional image.

More comprehensive and higher-quality updating will be achieved principally if a predefined area surrounding the partial areas covered by the new or eliminated image(s) is also updated during updating, particularly if interpolating takes place. So not only will the new original image data be used; a predefined area surrounding the partial area covered will also be updated by a new interpolation. The new image data of the newly recorded images will as a result slowly but surely update the entire reconstruction volume. Further conditions can also be considered in the updating of said type of the surrounding area. Thus it can be provided when the area surrounding the partial area covered by a new image is being updated only for those images from the basic set to be considered that were recorded within a specific period of time before the new image. That will preclude images that are too old being interpolated with the new images.

It can expediently be provided for assigned information to be stored for each voxel of the reconstruction volume, which information reproduces the images that have contributed to said voxel in the reconstruction, or for assigned information to be stored for each image, which information contains the reconstruction volume's voxels to which the image has contributed. That is because an image can particularly advantageously be deleted from the basic set and/or memory if no longer required for reconstructing, or a threshold can be defined for the voxels to which an image is contributing, upon the undershooting of which threshold the image will be deleted from the basic set and/or memory. That can be envisaged as being a third, deleting process that monitors the extent to which images in the basic set are still needed at all or whether they can now be eliminated. Very old images are, for example, owing to the updating operations taking place, often contributing only at very few places in the reconstruction volume. Said images will be identified and removed from the basic set, with, where applicable, updating taking place, during which said few voxels will be, for example, re-interpolated. Efficient memory management will be made possible thereby.

It is also possible for a deleting time to be determined relative to the present time and for images whose time of recording precedes the deleting time to be removed from the basic set and/or memory. That, too, can be done as part of the deleting process already mentioned above. Consequently, the only images retained will be those recorded within a specific period of time relative to the present time, for example the images recorded during the last 10 minutes. That embodiment also promotes efficient memory management.

Despite regular updating of the reconstruction volume, it remains to be stressed that it only ever takes place locally. Possibly even only original image data from areas covered by said images will be newly inserted into the reconstruction volume. It is therefore at least possible that the overall quality of the reconstruction will suffer after a certain period of time. A new-reconstruction condition can therefore expediently be provided on whose occurrence the reconstruction volume will be reconstituted completely afresh from the images in the basic set. New-reconstruction conditions of said type can be, for instance, the expiration of a new-reconstruction period and/or the recording of a specific number of new images. A certain sustained quality standard will be achieved thereby. It can in particular be provided in the case of new reconstructions of said type for the basic set to be re-determined from as up-to-date as possible images and for the remainder of the memory to be cleared again.

The choice of images belonging to the basic set can be dependent on the operational flow chosen for recording. If sufficiently good coverage of the target volume by the images recorded over a specific period of time is in each case insured solely by the recording method, then it can be provided for the basic set of images to be formed from all the images recorded during a specific period of time or one that can be specified based on the present time. If the images are available arranged chronologically in a list, then a continuous partial area of the list, for example, will be defined as the basic set. Catheters are, for example, known in which an image recording device automatically rotates periodically; or the catheter itself rotates. A "panoramic view" will then be obtained over one cycle.

It is alternatively possible for the basic set of images to be selected based on a criterion insuring optimal coverage of the target volume. From the mass of recorded images, those specifically providing even and complete coverage of the target volume will consequently be selected. As a further criterion it is therein expedient, in the case of images covering adjacent or identical partial areas of the target volume, to consider the time of recording, in particular preferably to include more recent images in the basic set. That alone will be of advantage in terms of up-to-dateness.

It can, for example, be of practical advantage in the case of a slow, step-by-step motion of the image recording device within the target volume, in which device said volume is being scanned step-by-step, for example, for the reconstruction volume to be dynamically enlarged when images outside the area of the previous reconstruction volume are being recorded. The reconstruction volume will accordingly slowly increase in size. That will be of practical advantage for example when, say, a blood vessel is to be recorded as the hollow organ and a catheter having an image recording device is moving slowly along said vessel. Continuous updating and, where applicable, expansion will then take place at the front end of motion, which is to say where the image recording device happens to be, while no new reconstructing will be necessary of the area situated further back that has already been recorded.

So that a certain quality can be guaranteed for the reconstruction, it can be provided for updating not to be performed until a specific number of images have been recorded overall.

Several possibilities have been provided for displaying the reconstruction volume which, being well known, are deemed not to require a detailed explanation here. Possibilities that can be instanced for three-dimensional displaying include "fly" visualizing of a reconstruction volume in an internal view and the "volume rendering" technique. It is equally possible to display two-dimensional sectional views of the reconstruction volume to the user, who has all manner of options, being able to select the view, rotate or zoom in on the reconstruction volume and possibly have specific areas highlighted, and choose from all kinds of further options.

It can, though, especially and to particular advantage be provided for the areas that have changed during updating or those that are covered by new images to be identified in the display in particular in color. That will make it possible to tell where updating operations have taken place and which areas of the reconstruction volume are thus most up-to-date. In a development a graduated display of the reconstruction's up-to-dateness can also be provided, for example color-coded. A user will thus also be able to tell in which areas there is, for example, out-of-date data, in order to access this, where applicable, using the image recording device for gathering new data. Through the up-to-dateness display in conjunction with the inventive method, the user will have not only a highly up-to-date display of the reconstruction volume but also further information about the relevant area's up-to-dateness.

It can expediently be just the same if an older reconstruction volume is shown along with the display of the updated reconstruction. Being given the opportunity to make a direct comparison, the user will be able to tell from a combined display of said type what changes have occurred in which area of the target volume.

The image recording device can be periodically moved automatically or manually and the basic set specified as being the images recorded over the last cycle. It is possible when hollow organs, in particular hollow vessels, are being recorded to use, for example, a rotating image recording device located in a catheter head. If the catheter moves only very slightly, then after one revolution the self-same partial area of the target volume recorded prior to a revolution will be recorded again. That image can then, for example, simply be replaced in the course of updating. That variant is particularly advantageous when the ring buffer is used. That is because it can therein be provided for the ring buffer to have exactly as many storage locations as images are recorded over a complete cycle. The entire contents of the ring buffer will then automatically be used as the basic set for reconstructing and an image showing a specific partial area of the target volume will always be filed at the same location in the ring buffer.

In particular an ultrasonic device can be provided as the image recording device. Intracardial echocardiography (ICE) devices have become established as a standard in the field of cardiac imaging. An OCT (optical coherence tomography) image recording device can, though, also be provided.

The parameters, thresholds, and settings cited hitherto can, of course, all be configured by the user, for example via a user interface. A user can specify, for example, how many newly recorded two-dimensional images there must be before the reconstruction volume is updated. Just as with the conditions or further condition, a user is likewise able to configure which new-reconstruction conditions are to result in a complete, new reconstruction. All other parameters of the method are, of course, also user-configurable.

BRIEF DESCRIPTION OF THE DRAWINGS

Further features and specifics of the invention will emerge from the exemplary embodiments described below and with reference to the drawings, in which.

DETAILED DESCRIPTION OF THE INVENTION

Figure 1:
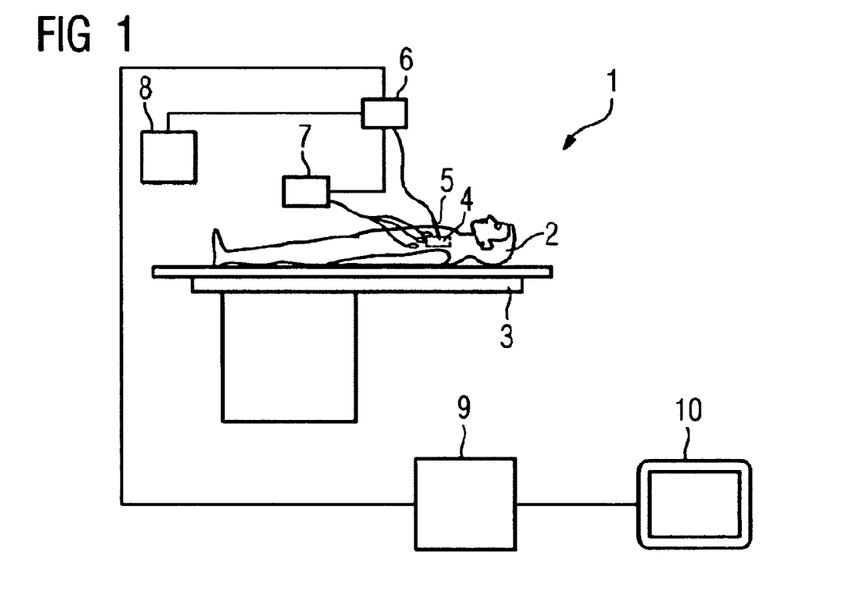
FIG. 1 shows a medical examination device embodied for carrying out the inventive method.

FIG. 1 shows a medical examination device 1. A patient 2 is therein located on a patient support 3, with the patient including a target volume 4 requiring to be recorded, here in particular in the cardial area, into which a catheter 5, including an image recording device, has already been inserted. The catheter 5 and the image recording device are controlled as appropriate by a catheter control device 6. An ECG device 7 records the ECG of the patient 2. The ECG device 7 sends its data to the catheter control device 6 so that triggered recording of two-dimensional images by the image recording device, here an ultrasonic device, can take place. The position and orientation of the image recording device of the catheter 5 at the time a two-dimensional image is recorded can be determined by means of a locating and navigating system indicated at 8. For each recorded two-dimensional image its position and orientation within the target volume 4 is recorded and stored. The images are then conveyed to a computing device 9. The images' position and orientation being already known, a reconstruction volume can be determined therefrom in the computing device 9. The computing device 9 is additionally embodied for performing locally limited updating of the reconstruction volume when certain conditions occur, with image recording continuing. The respectively up-to-date reconstruction volume can be displayed on a monitor 10.

Figure 2:
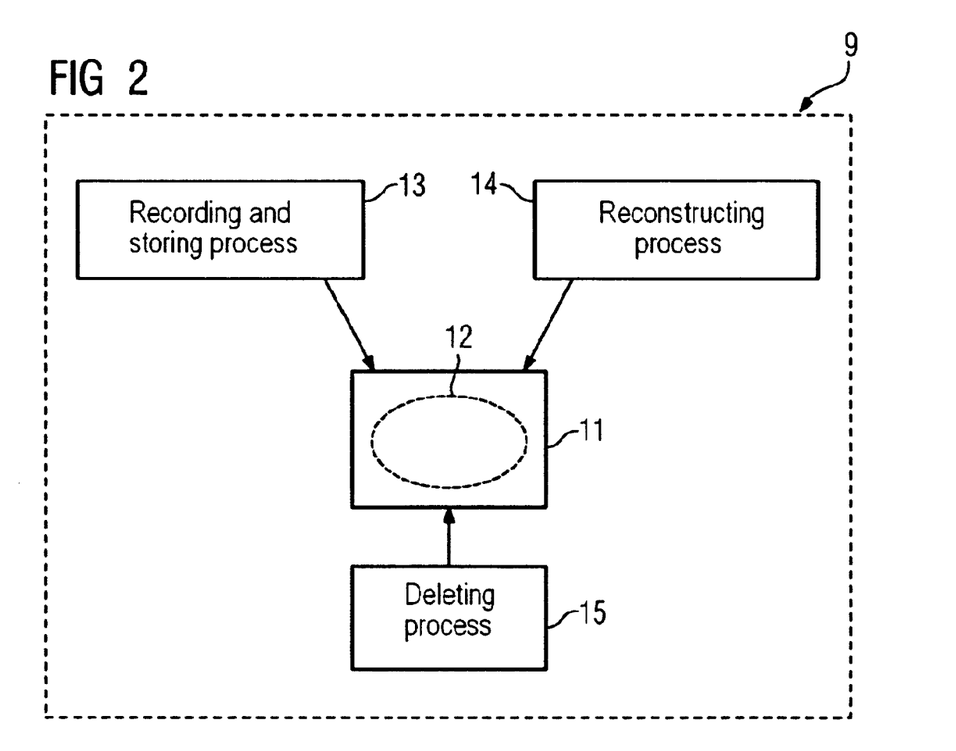
FIG. 2 is a general schematic sketch of the accessing of a memory by three processes running in parallel.

The operating mode of the computing device 9, which is to say the inventive method itself, is explained in more detail by means of FIG. 2. Provided inside the computing device 9 is a memory 11 in which the images' image data is filed. A basic set 12 containing the images currently used for the reconstruction volume will under certain criteria be determined from the images filed in the memory 11. Moreover, three different processes run in parallel in the computing device 9. A recording and storing process 13 controls the recording and storing of new images in the memory 11. A reconstructing process 14 produces or, as the case may be, updates the reconstruction volume. A deleting process 15 insures ideal memory management. All three processes 13, 14, and 15 simultaneously access the dynamic memory 11, whose size can be adjusted during operation. The processes 13, 14, and 15 will now be explained in more detail below.

Figure 3:
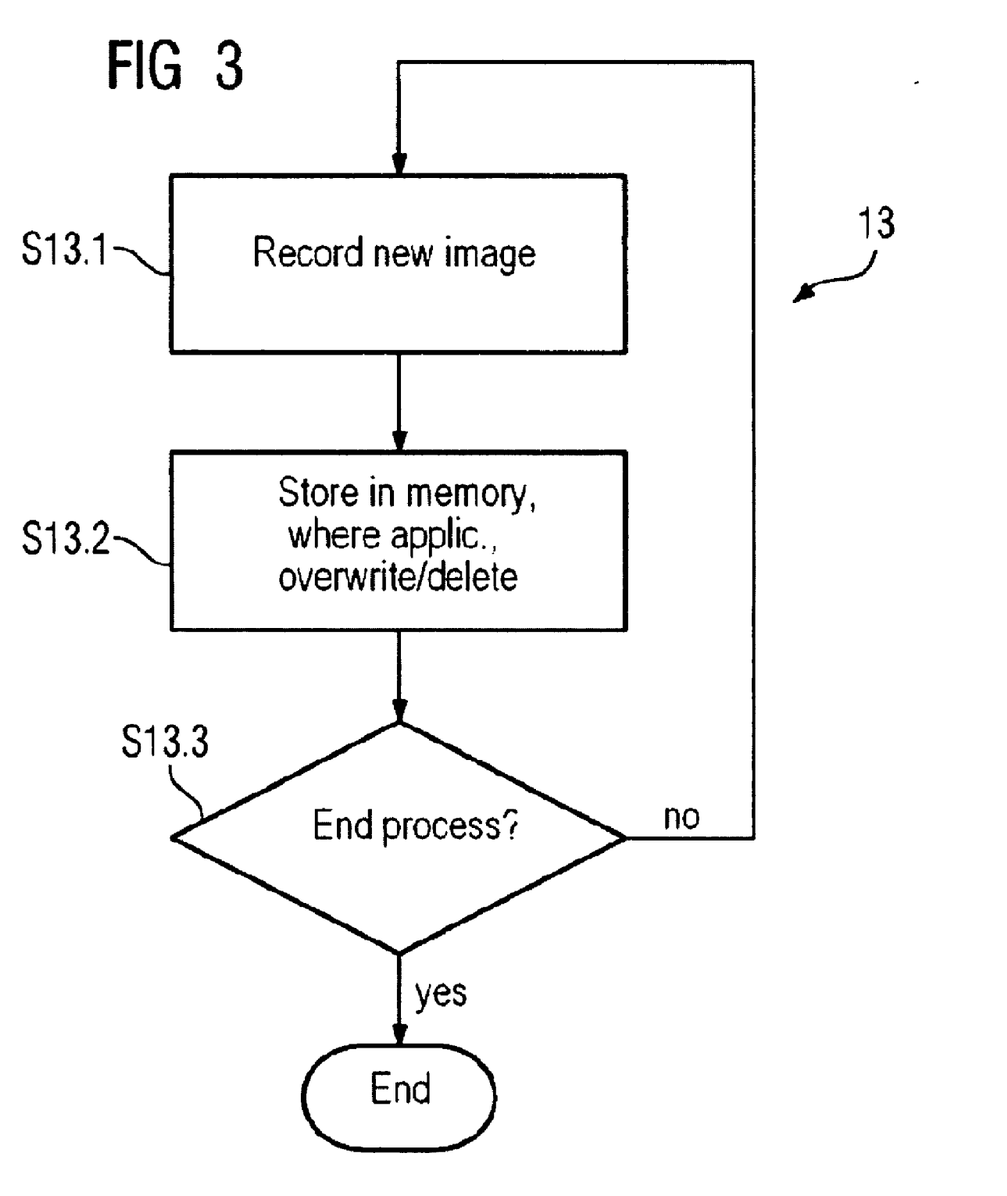
FIG. 3 is a flowchart of a recording and storing process.

FIG. 3 is a flowchart of the recording and storing process 13. New images are therein recorded continuously, step S13.1, in realtime, triggered, where applicable, by the ECG device 7. A newly recorded image of said type is then, at step S13.2, filed in the memory 11. The counter for recorded images is simultaneously incremented by one. If it has been provided that for each newly recorded image, starting from a fixed number of images present in the memory 11, another image, for example the oldest image present or an image sharing its orientation and position with the newly recorded image will be deleted, then that will also be done at step S13.2, with the eliminated image's memory location being overwritten with the newly recorded image. The counter for eliminated images will also, where applicable, be incremented. A check is then carried out at step S13.3 to determine whether the process, namely image recording, is to be ended. If not, then the next image will be recorded. If so, then the process 13 as well as the method and the other processes will be ended.

Figure 4:
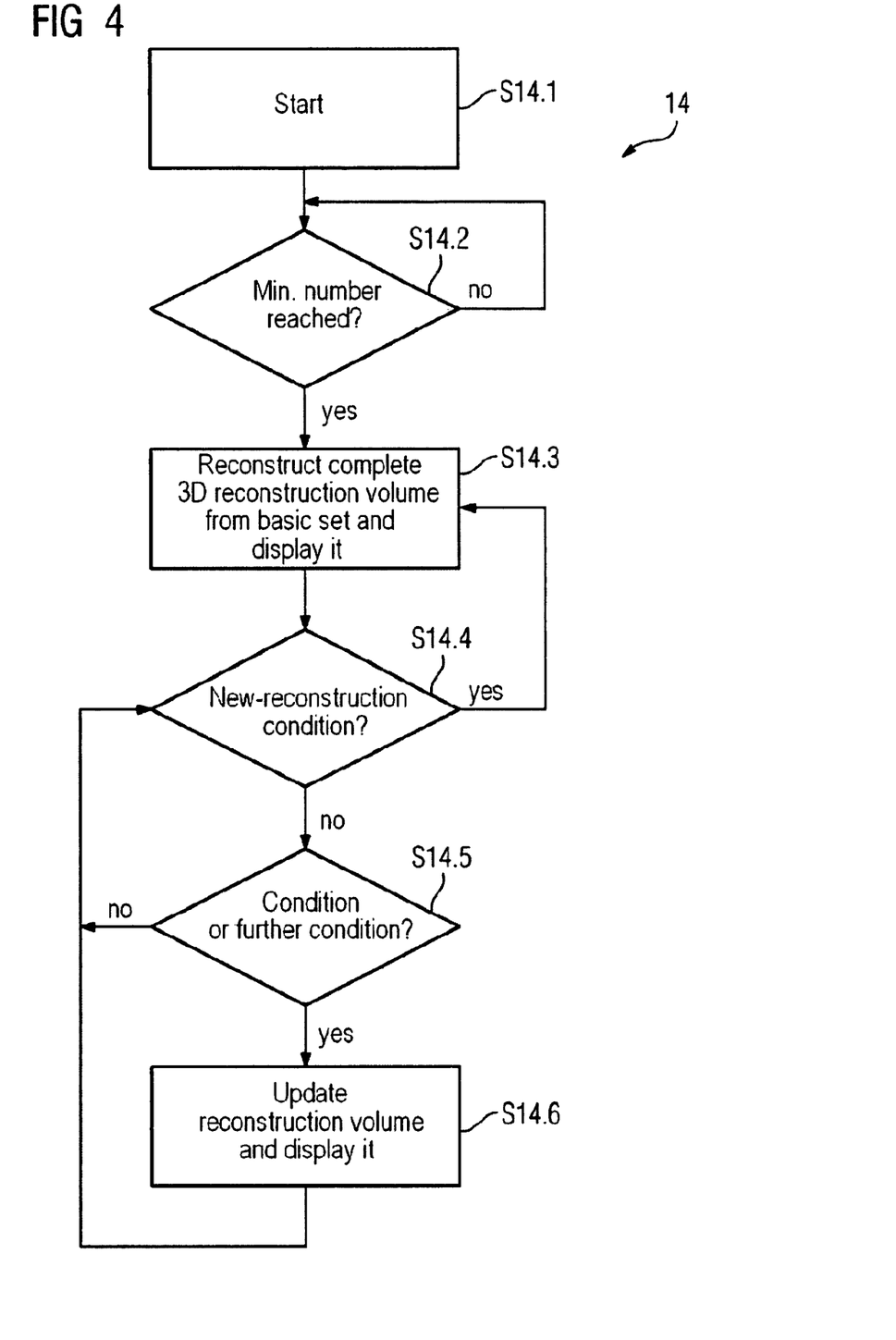
FIG. 4 is a flowchart of a reconstructing process.

FIG. 4 is a flowchart of the reconstructing process 14. The method starts at step S14.1, simultaneously with image recording, which is to say the recording and storing process 13. So that a first reconstruction can be carried out, meaning so that a reconstruction volume can be produced, there must first be a minimum number of recorded images in the memory 11. That is checked at step S14.2. If the minimum number has been reached, then the complete three-dimensional reconstruction volume will be reconstituted at step S14.3. At the start of the method the basic set 12 is, of course, still formed from all the images filed in the memory 11 when the minimum number has been reached. After said first reconstruction the reconstruction volume is displayed on the monitor 10. Several steps then follow that are repeated until the end of the method, meaning until the end of recording. A check is first carried out at step S14.4 to check whether the new-reconstruction condition, which is to say the condition for a completely new reconstruction of the reconstruction volume, is present. A condition of said type can be, for example, reaching a specific number of new images recorded since the last complete reconstruction. It is, of course, also possible to at regular intervals produce a completely new reconstruction of the reconstruction volume from the basic set. So if the new-reconstruction condition is present, the relevant counters will be reset and the complete reconstruction volume will at step S14.3 be reconstituted afresh from the basic set 12 and displayed.

The basic set 12 can therein be defined in various ways. For instance it is possible to use all the images recorded during a specific period of time. The criterion for including images in the basic set 12 can, though, also be maximally ideal coverage of the target volume 4. The time of recording can, however, also be taken into consideration therein as a further criterion.

If the new-reconstruction condition is not present at step S14.4, a check will next be carried out to determine whether the predefined condition or further condition for locally limited updating of the reconstruction volume is present at step S14.5. It is therein particularly possible to take recourse to the counting of the newly recorded or eliminated images or, as the case may be, to their sum. Updating can thus be performed in the case of there being a specific number of newly recorded images. Time-controlled updating is, of course, equally possible. If the condition has not been met, then the presence of the new-reconstruction condition will be re-checked at step S14.4. If, though, the condition or further condition has been met at step S14.5, then updating of the reconstruction volume and displaying of the reconstruction volume will take place at step S14.6 and the relevant counters will be reset.

Said locally limited updating which, being locally limited, requires less computing or processing time, can be carried out in various ways. For the reconstruction volume's locations at which there is new original image data it is on the one hand possible simply to enter said new original image data in the reconstruction volume, which is to say in the corresponding voxel. It is additionally possible, and with improved quality being achieved thereby, to define a fixed area surrounding the partial area of the reconstruction volume, which partial area is covered by the newly recorded or, as the case may be, eliminated image, and to carry out a new interpolation in said surrounding area including images from the basic set 12. The images from the basic set 12 that are used for interpolating in the surrounding area can therein be subject to further conditions. It can be provided, for example, for images recorded no longer than a predefined time before the newly recorded image under consideration or, as the case may be, eliminating of the old image to be used for said updating interpolation.

Figure 5:
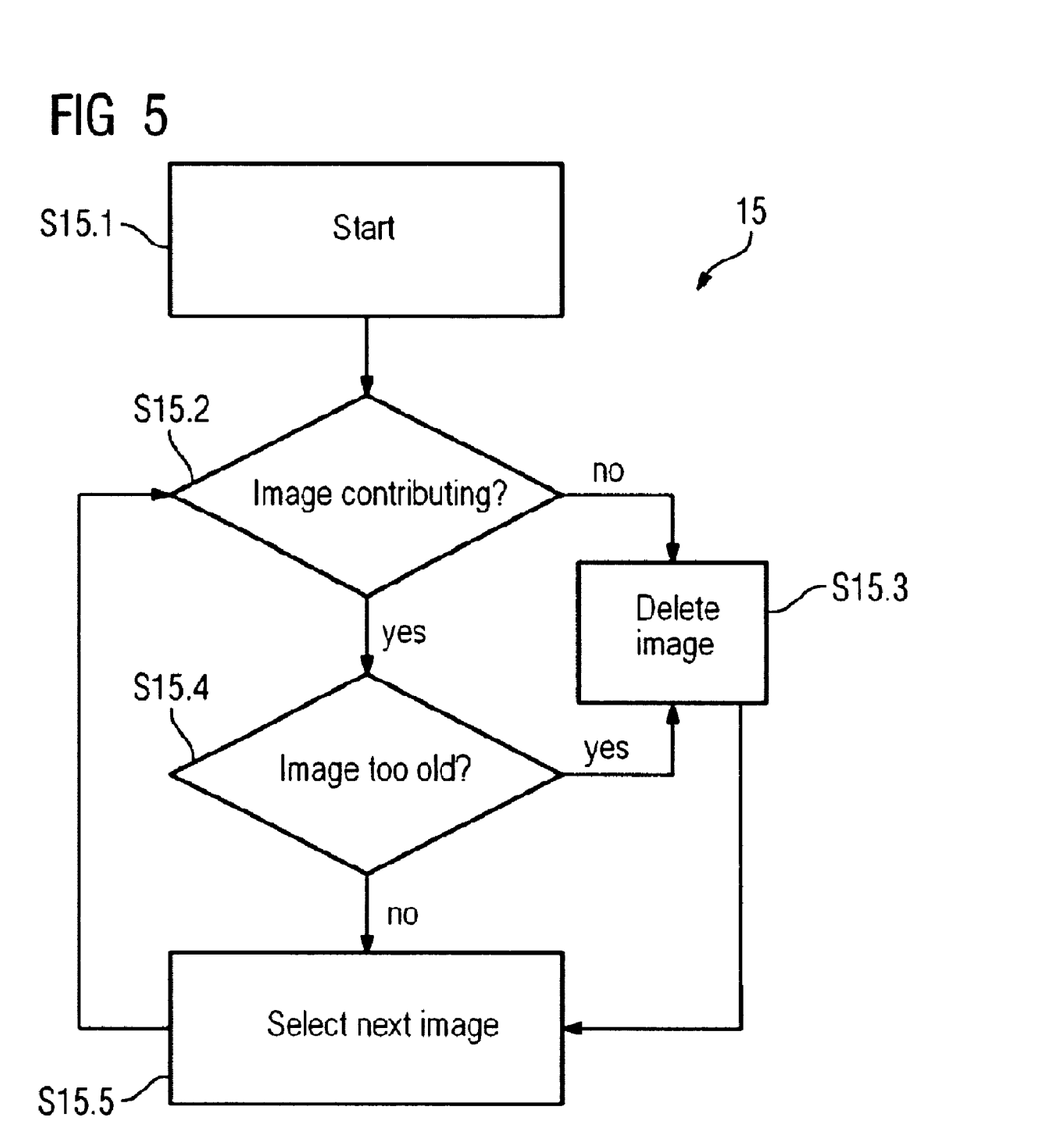
FIG. 5 is a flowchart of a deleting process.

FIG. 5 is a flowchart of the deleting process 15. That is a process, designed for optimizing memory management, which runs continuously in the background after the start of the method at step S15.1. A check is therein first carried out at step S15.2 to determine whether or to what extent the image presently under consideration is contributing to the reconstruction volume. It is of course necessary here for the contribution to be determinable. For that purpose it is expediently provided for the reconstruction volume's voxels to which the image is contributing to be stored for each image.

It is, of course, alternatively also possible to, for each voxel of the reconstruction volume, store which image has contributed thereto, then count the number of occurrences of said image that is being considered at that time. If an image from the basic set 12 is no longer needed at all for the reconstruction volume, or if the number of voxels to which said image is contributing has fallen below a predefined threshold, then the image can be removed from the basic set 12 and the memory 11, step S15.3. If a threshold has not been undershot, meaning if a contribution is still being made to the reconstruction volume, then the counter for eliminated images will herein, where applicable, be incremented by one.

A check is carried out at the next step, S15.4, to determine whether the image being considered is, where applicable, exceeding an age limit, meaning whether it is too old. That will prevent images that are too old from remaining in the basic set 12 or the memory 11. If the image is too old it will be deleted at step S15.3. Whatever the case, whether the image being considered is deleted or not, the next image will then be selected at step S15.5 and the conditions therefor examined.

Figure 6:
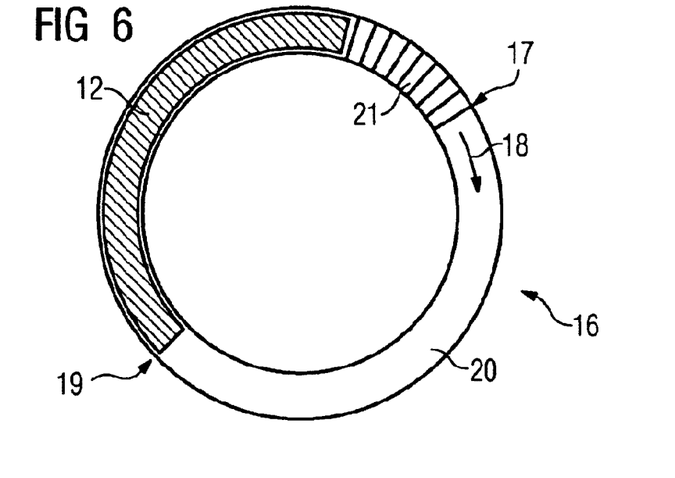
FIG. 6 shows a ring buffer as an example of implementing the memory.

FIG. 6 shows a ring buffer 16 as an example of implementing a memory 11. Newly recorded images are therein filed by the recording and storing process 13 at the position of the write pointer 17, as a result of which an old image will be overwritten. As indicated by the arrow 18, old images are in this direction always overwritten by newly recorded images. The images are arranged in the ring buffer 16 according to time of recording, and the basic set 12 is formed from consecutive images within a specific recording period. In FIG. 6 the read pointer 19 is at the beginning of the basic set 12 at the start of a complete new reconstruction of the three-dimensional reconstruction volume. Stored between the read pointer 19 and the write pointer 17 are even older images 20 that are no longer contributing to the reconstruction volume. Between the end of the basic set 12 and the write pointer 17 are newly recorded images 21 not yet being fed into the reconstruction volume because the conditions for updating the reconstruction volume have not yet been met.

Figure 7:
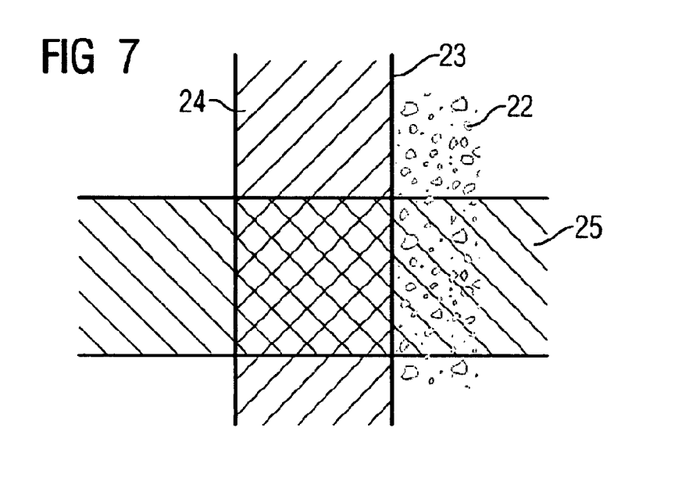
FIG. 7 is an example of displaying a section through the reconstruction volume.

FIG. 7 shows, as an example of displaying a reconstruction volume, a section through a cardiac wall of the patient 2. To be seen are the blood 22, the endocardium 23, and the myocardium 24. Shown in color at 25 is an area that was recently also updated while the reconstruction volume was being updated; the coverage area, therefore, of a newly recorded image and its defined surrounding area.

Figure 8:
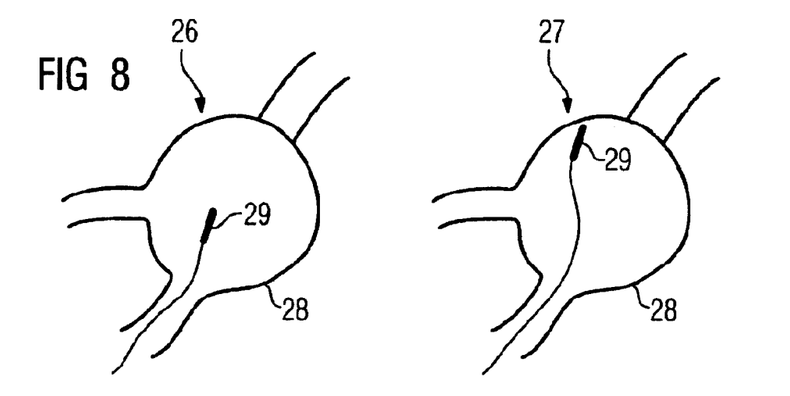
FIG. 8 shows displaying of the current reconstruction volume alongside an older reconstruction volume.

As shown in FIG. 8, reconstruction volumes 26 and 27 produced at different times can also be displayed next to each other in parallel. The reconstruction volume 27 is therein the more up-to-date volume. Both displays show the heart ventricle 28 of the patient 2 at different times. Also to be seen in the display is an intervention catheter 29. Thanks to displaying of both reconstruction volumes 26 and 27 in parallel, the user is able to tell that the intervention catheter has since moved on from its position in the reconstruction volume 26 to a new position in the new reconstruction volume 27. The occurrence of lesions, for example, can also be visualized in this manner.

Via a user interface that can also be displayed on the monitor 10 the user is able to change parameters, conditions, and thresholds in such a way that they will be ideally suited for the procedure requiring to be performed. It is therein in particular possible also to spatially limit, for example, the threshold for updating in the case of newly recorded images. It can then be provided, for example, for updating of the reconstruction volume not to take place generally for, for example, five new recorded images but only when there are five newly recorded images showing the area of the intervention catheter 29. The user can therefore select a subvolume of particular interest, even if it may move during the procedure.

The invention claimed is:

1. A method for reconstructing a three-dimensional image of a target volume of a human body in realtime during a medical procedure, comprising:
    recording a plurality of two-dimensional images of the target volume by an image recording device;
    selecting a basic set from the recorded images comprising a minimum number of two-dimensional images;
    determining the three-dimensional reconstruction volume from the basic set;
    recording a new image of the target volume by the image recording device;
    locally limited updating a partial area of the reconstruction volume covered by the new image under a condition; and
    displaying the updated reconstruction volume,
    wherein the recorded images are filed in a memory,
    wherein the images are filed in the memory in an order according to a recording time,
    wherein a size of the memory is adjusted,
    wherein a defined subset of the filed images is selected as the basic set,
    wherein each recorded image comprises an assigned information that comprises a voxel of the reconstruction volume to which the image has contributed, and
    wherein a threshold is defined for the voxel to which the image has contributed and the image is deleted from the basic set or the memory if the threshold is undershot.

2. The method as claimed in claim 1,
    wherein the memory is a ring buffer, and
    wherein the basic set is selected as a sequence of images filed in a specific section of the ring buffer or in a section that is specified based on the new image.

3. The method as claimed in claim 1,
    wherein the basic set or the memory comprises a fixed number of images,
    wherein when the new image is added in the basic set or the memory, an image is eliminated from the basic set or the memory if the fixed number has been reached, wherein the eliminated image is an oldest image in the basic set or the memory, wherein a partial area of the reconstruction volume covered by the eliminated image is locally limited updated under a further condition, and wherein the updated reconstruction volume is displayed.

4. The method as claimed in claim 3, wherein the condition or the further condition for updating is a specific number of newly recorded or eliminated images or a specific period of time, and wherein the updating takes place for each newly recorded or eliminated image or when an image has been newly recorded or eliminated within the specific period of time.

5. The method as claimed in claim 3, wherein a predefined area surrounding the partial areas covered by the new or the eliminated image is updated, wherein the predefined area is updated by interpolating the new image, wherein the interpolating is performed with images recorded within a specific period of time before the new image is recorded.

6. The method as claimed in claim 1, wherein the new image covers an area lying at least partially within a defined subvolume of the target volume, wherein the subvolume of the target volume is in a vicinity of the image recording device within the target volume.

7. The method as claimed in claim 1, wherein an image data in an area of the reconstruction volume covered by the new image is replaced with a corresponding image data of the new image.

8. The method as claimed in claim 1, wherein a deleting time is determined relative to a present time and images recorded before the deleting time is eliminated from the basic set or the memory.

9. The method as claimed in claim 1, wherein the reconstruction volume is reconstructed completely from the basic set if a new reconstruction condition has been met, wherein the new reconstruction condition is an expiration of a new reconstruction period or a specific number of newly recorded images.

10. The method as claimed in claim 1, wherein the basic set comprises all images recorded during a specific period of time.

11. The method as claimed in claim 1, wherein the basic set is selected from the recorded images based on a criterion of optimal coverage of the target volume, wherein a further criterion of recording time is considered in selecting the basic set if a plurality of images cover adjacent or identical partial area of the target volume, and wherein a more recent image is selected in the basic set.

12. The method as claimed in claim 1, wherein the reconstruction volume is dynamically enlarged if the new image is outside an area of a previous reconstruction volume.

13. The method as claimed in claim 1, wherein the updating is not performed until a specific number of images have been recorded overall.

14. The method as claimed in claim 1, wherein an updated area or the partial area covered by the new image is identified in the display of the updated reconstruction by a color, and wherein a previous reconstruction volume is displayed along with the display of the updated reconstruction.

15. The method as claimed in claim 1, wherein the image recording device is periodically moved automatically or manually and the basic set is selected from images recorded over a last cycle.

16. The method as claimed in claim 1, wherein the images are recorded by the image recording device within the target volume, wherein the image recording device is an ultrasonic device, and wherein the ultrasonic device is an intracardial echocardiography device.

17. A medical device for reconstructing a three-dimensional image of a target volume of a human body in realtime during a medical procedure, comprising:

an image recording device that records a plurality of two-dimensional images of the target volume; and a computing device that:

selects a basic set from the recorded images comprising a minimum number of two-dimensional images, determines the three-dimensional reconstruction volume from the basic set, and locally limited updating a partial area of the reconstruction volume covered by a newly recorded image, wherein the recorded images are filed in a memory, wherein the images are filed in the memory in an order according to a recording time, wherein a size of the memory is adjusted, wherein a defined subset of the filed images is selected as the basic set, wherein each recorded image comprises an assigned information that comprises a voxel of the reconstruction volume to which the image has contributed, and wherein a threshold is defined for the voxel to which the image has contributed and the image is deleted from the basic set or the memory if the threshold is undershot.

* * * * *